(12) United States Patent
Daich

(10) Patent No.: US 9,999,691 B2
(45) Date of Patent: Jun. 19, 2018

(54) METHOD FOR THE DETECTION OF ENZYMATIC ACTIVITY WITH MAGNETICALLY FUNCTIONALIZED SUBSTRATES

(71) Applicant: Julian Daich, Toledo (ES)

(72) Inventor: Julian Daich, Toledo (ES)

(*) Notice: Subject to any disclaimer, the term of this patent is extended or adjusted under 35 U.S.C. 154(b) by 679 days.

(21) Appl. No.: 14/140,499

(22) Filed: Dec. 25, 2013

(65) Prior Publication Data
US 2014/0162286 A1   Jun. 12, 2014

Related U.S. Application Data

(63) Continuation of application No. 13/009,867, filed on Jan. 20, 2011, now abandoned.

(60) Provisional application No. 61/297,613, filed on Jan. 22, 2010.

(51) Int. Cl.
| G01N 33/573 | (2006.01) |
| A61K 49/08 | (2006.01) |
| A61K 49/18 | (2006.01) |
| B82Y 5/00 | (2011.01) |
| A61K 49/14 | (2006.01) |
| C12Q 1/37 | (2006.01) |

(52) U.S. Cl.
CPC ............ *A61K 49/14* (2013.01); *A61K 49/085* (2013.01); *A61K 49/1848* (2013.01); *A61K 49/1863* (2013.01); *B82Y 5/00* (2013.01); *C12Q 1/37* (2013.01); *G01N 33/573* (2013.01); *G01N 2333/96425* (2013.01)

(58) Field of Classification Search
None
See application file for complete search history.

(56) References Cited

U.S. PATENT DOCUMENTS

2008/0044360 A1\*  2/2008  Caravan ............... A61B 5/055
424/9.341

OTHER PUBLICATIONS

Lebel et al. Novel solubility-switchable MRI agent allows the noninvasive detection of matrix metalloproteinase-2 activity in vivo in a mouse model. 2008 Magn. Reson. Med. 60: 1056-1065.\*

(Continued)

*Primary Examiner* — Michael G Hartley
*Assistant Examiner* — Jennifer Lamberski
(74) *Attorney, Agent, or Firm* — Roach Brown McCarthy & Gruber, P.C.; Kevin D. McCarthy

(57) ABSTRACT

The present invention provides methods for detecting an enzymatic activity, the method including combining at least one magnetic particle to an enzyme substrate to form a magnetically modified substrate, reacting the magnetically modified substrate with at least one enzyme; and detecting a change in a magnetic property of the magnetically modified substrate or its cleavage products, thereby detecting an activity of said at least one enzyme, wherein the method may be applied to a human subject to detect a disease selected from the group consisting of rheumatitis, arthritis, an injury, Dupuytren's disease, Peyronie's disease, a collagen related disease, steatosis, fibrosis, cirrhosis, metastasis, tissue regeneration, cancer, coronary disease, a liver disease, a metabolic condition, an infection and an inflammatory disease.

20 Claims, 5 Drawing Sheets

(56) References Cited

OTHER PUBLICATIONS

Gupta et al. Synthesis and surface engineering of iron oxide nanoparticles for biomedical applications. 2005 Biomaterials 26: 3995-4021.*

Xuan et al. Tuning the grain size and particle size of superparamagnetic Fe3O4 microparticles. 2009 Chem. Mater. 21: 5079-5087.*

Zhao et al. Magnetic sensors for protease assays. 2003 Angew. Chem. Int. Ed. Engl. 42: 1375-1378.*

Perez et al. Magnetic relaxation switches capable of sensing molecular interactions. 2002 Nat. Biotechnol. 20: 816-820.*

Swaminathan S, Gadolinium toxicity: Iron and ferroportin as central targets, Magn Reson Imaging (2016), http://dx.doi.org/10.1016/j.mri.2016.08.016.

Alain Roch, Yves Gossuin, Robert N. Muller, Pierre Gillis, Superparamagnetic colloid suspensions: Water magnetic relaxation and clustering; J. Magnet. Magnetic. Mater. vol. 293 (2005) 532-539.

Tassa et al., Dextran-Coated Iron Oxide Nanoparticles: a Versatile Platform for Targeted Molecular Imaging, Molecular Diagnostics and Therapy; Acc Chem Res. Oct. 18, 2011; 44(10): 842-852. doi:10.1021/ar200084x. (20 pages).

Josephson et al., High-Efficiency Intracellular Magnetic Labeling with Novel Superparamagnetic-Tat Peptide Conjugates, Bioconjugate Chem. 1999,10, 186-191 (6 pages).

Roch et al., Superparamagnetic colloid suspensions: Water magnetic relaxation and clustering, Journal of Magnetism and Magnetic Materials 293 (2005) 532-539 (8 pages).

Woessner, Matrix metalloproteinases and their inhibitors in connective tissue remodeling, The FASEB Journal, vol. 5 May 1991 (10 pages).

Kobayashi et al., Amino-silane Modified Superparamagnetic Particles with Surface-Immobilized Enzyme, Journal of Colloid and Interface Science, vol. 141, No. 2, Feb. 1991 (7 pages).

Steven, Single-stage partial depolymerisation of collagen fibrils, Biochimica et Biophysica Acta, 130 (1966) 196-201 (6 pages).

Walker, Macromolecular drug delivery: methods and protocols, vol. 480 from Methods in molecular biology, Springer protocols (2009) (207 pages).

Ayad et al., The Extracellular Matrix Facts Book, (1998) (299 pages).

Mitchell et al., MRI principles, 2004 (207 pages).

Kielty et al, The Collagen Family: Structure, Assembly, and Organization in the Extracellular Matrix, Connective Tissue and Its Heritable Disorders, pp. 159-221 (2002) (63 pages).

* cited by examiner

METHOD FOR THE DETECTION OF ENZYMATIC ACTIVITY WITH MAGNETICALLY FUNCTIONALIZED SUBSTRATES

CROSS-REFERENCE TO RELATED APPLICATIONS

The present application claims priority from U.S. provisional patent application No. 61/297,613 to Daich, filed on Jan. 22, 2010, entitled "Method for the diagnosis of enzymatic activity with magnetically functionalized substrates" and incorporated herein by reference in its entirety.

FIELD OF THE INVENTION

The present invention relates generally to a method for the diagnosis of enzymatic activity by means of the measurement of magnetic properties of functionalized substrates.

BACKGROUND OF THE INVENTION

Enzymes are proteins which catalyze chemical reactions. In enzymatic reactions, the molecules upon which an enzyme acts are called substrates, and the enzyme converts them into different molecules called the products. Enzymes are usually very specific as to which reactions they catalyze and the substrates that are involved in these reactions.

The internal dynamics of enzymes is connected to their mechanism of catalysis. Internal dynamics are the movement of parts of the enzyme's structure, such as individual amino acid residues, a group of amino acids, or even an entire protein domain. These movements occur at various time-scales ranging from femtoseconds to seconds. Networks of protein residues throughout an enzyme's structure can contribute to catalysis through dynamic motions.

Protein motions are vital to many enzymes, but whether small and fast vibrations, or larger and slower conformational movements are more important depends on the type of reaction involved. Complementary shape, charge and hydrophilic/hydrophobic characteristics of enzymes and substrates are responsible for this specificity. Enzymes can also show impressive levels of stereospecificity, regioselectivity and chemoselectivity. The tight control of enzyme activity is essential for homeostasis, any malfunction (mutation, overproduction, underproduction or deletion) of a single critical enzyme can lead to disease. The importance of enzymes is shown by the fact that a lethal illness can be caused by the malfunction of just one type of enzyme out of the thousands of types present in the organism.

Several clinical conditions, such as unstable plaque, metastasis, tissue regeneration, etc. are related to enzymatic disorders.

Most biological matter is diamagnetic in nature having negative magnetic susceptibility. For the purposes of the present invention, magnetic particle are defined as any non diamagnetic composition of particles, crystals, molecules or ions. These particles attached to a protein will produce a magnetic signature different from that of the protein itself. Such magnetic signature is a function of the size and shape of the particles. Magnetization of a given material is defined as its average magnetic moment per unit volume and is determined by their internal structure and composition. Some magnetic particles of interest are the paramagnetic, superparamagnetic and ferromagnetic particles which are commonly utilized as contrast agents as single particles, microencapsulated in matrices or attached to other molecules. These magnetic agents are designed to maintain their magnetic properties constant over measurements and produce imaging effects according to their concentration and distribution at different body compartments and tissues.

There thus remains an unmet need to develop diagnostic methods for diagnosing or detecting diseases which are related to enzymatic disorders and further to develop methodologies for monitoring the progression of these diseases in mammalian subjects.

SUMMARY OF THE INVENTION

It is an object of some aspects of the present invention to provide a method to diagnose enzymatic activity by means of providing magnetically functionalized substrates as reporters of enzymatic activity, and measuring the magnetic properties of the functionalized substrates and their derived products. To achieve this objective non diamagnetic particles are selectively attached to specific substrates of interest.

The general basis of the present invention resides in a method for detecting an enzymatic activity in a living organism, the method comprising:
a) combining at least one magnetic particle to a substrate to form a modified substrate;
b) providing the modified substrate to a living organism; and
c) performing a measurement related to the magnetic properties of the modified substrate;
thereby diagnosing a metabolic or enzymatic activity occurring in said living organism.

The measurement may be performed by a method such as magnetic resonance imaging (MRI). According to some embodiments, the substrate is collagen.

There is thus provided according to an embodiment of the present invention, a method for detecting an enzymatic activity, the method including;
a) combining at least one magnetic particle to an enzyme substrate to form a magnetically modified substrate;
b) reacting the magnetically modified substrate with at least one enzyme; and
c) detecting a change in a magnetic property of the magnetically modified substrate or its cleavage products,
thereby detecting an activity of the at least one enzyme.

According to an embodiment of the present invention, at least one of such at least one magnetic particle is a superparamagnetic particle.

Additionally, according to an embodiment of the present invention, the change in the magnetic property is at least a partial change from superparamagnetic to paramagnetic.

Furthermore, according to an embodiment of the present invention, the detecting step includes detecting at least one relaxation time of the magnetically modified substrate or its cleavage products.

Moreover, according to an embodiment of the present invention, the least one relaxation time includes a first relaxation time prior to the reacting step and a second relaxation time after the reacting step.

Further, according to an embodiment of the present invention, the detecting step is performed by at least one of magnetic resonance, magnetic resonance imaging (MRI), electronic paramagnetic resonance (EPR), magnetometry, Mössbauer spectrometry, electromagnetic inductance, atomic force microscopy, magnetorelaxometry and a combination thereof.

Yet further, according to an embodiment of the present invention, the detecting step includes the use of at least one of a fine probe and a contrast agent in an imaging process.

Additionally, according to an embodiment of the present invention, the imaging process includes detecting at least one of a signal intensity, T1, T2, diffusion and a response to a saturation signal.

Moreover, according to an embodiment of the present invention, wherein the imaging process includes detecting at least one change in a signal intensity, T1, T2, diffusion and a response to a saturation signal measured a) before the reacting step and b) after the reacting step.

Additionally, according to an embodiment of the present invention, the change is indicative of at least one of;
 a. aggregation of the at least one magnetic particle;
 b. aggregation of the magnetically modified substrate;
 c. a change in particle size of the at least one magnetic particle; and
 d. a change in particle size of the magnetically modified substrate.

Furthermore, according to an embodiment of the present invention, the enzyme substrate includes at least one of; a protein, a polypeptide, a modified protein, a modified polypeptide, glycoprotein, collagen, fibrillin, elastin, laminin, osteocalcin, osteonectin, osteopontin and gelatin.

Additionally, according to an embodiment of the present invention, the at least one enzyme includes at least one of a metal-dependent enzyme, a protease, a lipase, a lipoprotein lipase, a hormone sensitive lipase, a metalloprotease, a matrix metalloproteinases (MMP), a collagenase and a gelatinase.

Moreover, according to an embodiment of the present invention, the reacting step is performed in vivo.

Additionally, according to an embodiment of the present invention, the reacting step is performed in a human subject in order to detect a disease or disorder associated with the activity of the at least one enzyme.

Further, according to an embodiment of the present invention, the disease or disorder is selected from the group consisting of a connective tissue related disease, rheumatitis, arthritis, an injury, Dupuytren's disease, Peyronie's disease, an extracellular matrix related disease, a collagen related disease, steatosis, fibrosis, cirrhosis, metastasis, tissue regeneration, cancer, coronary disease, a liver disease, a metabolic condition, an infection and an inflammatory disease.

There is thus provided according to another embodiment of the present invention, a method for detecting a disease in a human subject, the method including;
 a) combining at least one magnetic particle to a reactant to form a magnetically modified reactant;
 b) reacting the magnetically modified reactant with at least one enzyme in the human subject; and
 c) detecting a change in a magnetic property of the magnetically modified reactant thereby detecting the disease in the human subject.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows changes in nuclear magnetic relaxation as a function of particle size or state of aggregation, in accordance with an embodiment of the present invention;

FIG. 2 represents the M-H curve of type IV collagen functionalized with superparamagnetic magnetite nanoparticles with a diameter of 15 nm in 10 ml of saline suspension immobilized in agarose, in accordance with an embodiment of the present invention;

FIG. 3 represents the H-M curve of a similar suspension immobilized in agarose after incubation with type I collagenase for 12 h at 37° C., in accordance with an embodiment of the present invention;

Figure 4:
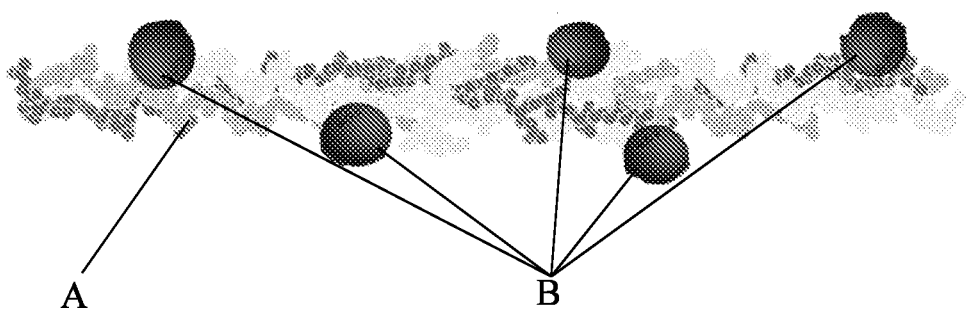
Figure 5:
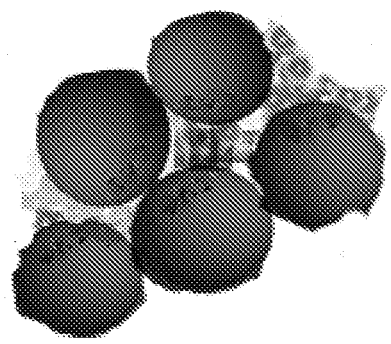

FIG. 4 shows a scheme of a modified collagen triple helical region, A, functionalized with magnetite nanoparticles, B, in accordance with an embodiment of the present invention; and FIG. 5 shows the effect of collagenolytic activity on the distribution of magnetic nanoparticles first immobilized on collagen after such collagen is digested by collagenases, in accordance with an embodiment of the present invention.

DETAILED DESCRIPTION OF THE INVENTION

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

An example of such kind substrate is collagen. Collagen has a complex structure. Its precursor protein (monomer) is called tropocollagen and measures about 300 nanometers in length and 1.4 nm in diameter. The tropocollagen is composed of three polypeptide chains called alpha chains which turn to form a triple helical structure. Each string constituted by a chain is a polypeptide, formed by a repetition of triplets in tandem containing amino kid glycine and is very rich in proline and hydroxyproline. The hydroxyproline is about 10 to 12% of all residue composition of collagen, being such percentage depending on the type of collagen. Each chain has a molecular weight of about 100000 Da. Collagen, in fact, is the substrate of several enzymes of the family of matrix metalloproteinases (MMP) that play several main functions in the construction and renovation of tissues. MMPs activity is associated with diseases such as arthritis, rheumatitis, conditions related with the growth of connective tissue as Dupuytren's or Peyronie's diseases, conditions that lead to liver fibrosis, cirrhosis or cardiovascular as the obstructions of the type unstable angina. A more complete description of the role of enzymatic activity in those diseases is given by Woessner J F Jr., 1991. Most of the diagnostic tests currently used in the assessing these pathologies or their progress are based on biopsies which involve high costs and risks.

Therefore, the determination in vivo of the collagenolytic activity of such enzymes, often called collagenases, are of great scientific and clinical interest. Collagenolytic activity of some MMPs derives some of its tertiary structure. These molecules are calcium and zinc dependent, much smaller that tropocollagen and have three distinct regions. One of them, called propeptidic, has the ability to join the chains of collagen. Another region, known as catalytic has the capacity to roll out the collagen's triple helix. The third area is the extreme carboxyl terminus, consisting of four β sheets that serve as the propeller blades pushing the enzyme, and cooperating in the dismemberment of the three chains in alpha helix. Then the alpha chains are freed and digested by other enzymes such as pepsin or trypsin.

In order to detect the collagenolytic activity of the enzymes of interest it is fundamental and necessary that the collagen will retain its tertiary triple helical structure during the process of immobilizing over collagen residues magnetic particles. Therefore the whole process should be done in a way that does not alter collagen's structure.

To understand the effect of aggregation of magnetic particles an overview of the properties of the different magnetic materials that can compose them is given first.

Ferromagnetic materials generally contain transition-metals as for example iron (Fe), magnesium (Mg), manganese (Mn), cobalt (Co), nickel (Ni), zinc (Zn) or copper (Cu). Ferromagnetic materials are also characterized by being made up of clusters of $10^{17}$ to $10^{21}$ atoms called magnetic domains, that all have their magnetic moments (spin populations) pointing in the same direction. The moments of the domains are random in non-magnetized materials, and point in preferred directions in magnetized materials. The ability to remain magnetized when an external magnetic field is removed is a distinguishing factor compared to paramagnetic, superparamagnetic, and diamagnetic materials.

Antiferromagnetism results when paramagnetic materials are placed in a external magnetic field at temperatures below a given temperature called transition temperature causing, some of the spins to aligned with the applied field and some to aligned against the field. For ferromagnetic materials the difference between those spin populations is not equal, so a resultant magnetization is present. The spins' coupling is not very strong, so when the external magnetic field is removed, thermal shaking causes the spins to return to the random state. Thus, there is no remnant or permanent magnetization present. All iron particles based on magnetite are either ferrimagnetic or ferromagnetic at physiological temperatures (transition temperature of iron particles is close to 850 Kelvin).

Superparamagnetic materials consist of individual domains of elements that have ferromagnetic properties in bulk. Their magnetic susceptibility is between that of ferromagnetic and paramagnetic materials. Superparamagnetic materials have the special property to behave as ferromagnetic materials under the effects of external magnetic fields but have paramagnetic characteristics wherein not resultant external magnetic is present or it does not have the necessary strength to cause the former effect. These materials are usually compositions that include crystals of few nanometers of ferromagnetic materials or nanocomposites magnets.

In order to fully understand superparamagnetism, the concept of anisotropy must be addressed. If a large number of paramagnetic ions are arranged in an orderly fashion the spins will interact so that when placed in an external field, the resultant magnetization is not longer isotropic. Anisotropy, therefore, describes the fact that the coupled-spins may align in more than one direction relative to the external field. For crystals of magnetite there are six possible anisotropic axes. Thus, under the effect of an magnetic field, the result would be six different energy values, with lowest and highest energies in directions that are parallel or antiparallel to such external field respectively. Since in suspensions the movement or motion of the crystals causes an averaging of the anisotropic energy, normally only the lowest energy axis is relevant.

Fundamental to the theory of superparamagnetic materials is the destabilizing effect of temperature on their magnetism. Thermal energy prevents the alignment of the magnetic moments present in superparamagnetic particles. After the removal of an applied magnetic field, the magnetic moments of superparamagnetic materials still exist but they are in rapid motion. Temperature also limits the magnetization of superparamagnetic materials produced by an applied magnetic field. At the temperatures of biological systems and in the applied magnetic fields of NMR imagers, superparamagnetic materials are less magnetic than their ferromagnetic counterparts.

Properties such as ferro- or ferri-magnetism are not intrinsic to a molecule or an ion but arise from a cooperative solid-state (bulk) behavior. Such properties are a consequence of the interactions between the molecules or ions and hence, methods to predict, control and modulate the solid state structure are essential to the understanding and manipulation of such behavior.

Some nanomaterials, such as nanoparticles in colloidal suspensions, are expected to exhibit unusual chemical and physical properties different from those of either the bulk solids or single particles. For materials made up of large crystals (diameters greater than 14 nm), the spins are divided and aligned within small magnetic domains called Weiss-domains. The direction of individual spins adopt the same direction along the anisotropic axes; the anisotropic energy is at minimum value and the system may be considered isotropic. This explains why ferromagnetic crystals of magnetite must be magnetized by placement into an external field in order to gain permanent magnetism. If crystals of magnetite are smaller than the Weiss-domains then superparamagnetism may be observed. In order to move from anisotropic axis to another the spin requires an input energy equal to the desired transition. The anisotropic energy is referred as KV where K is the anisotropy constant and V is the crystal volume. The distance between various crystals influences the KV since crystals in close proximity to each other may allow interactions between the spins resulting in the increase of KV. The flipping of the spins along the same axis in which an external field is applied is defined by the Nèel relaxation time, or $\tau_N$ and it is the result of the thermal agitation of the crystals. The Nèel relaxation time $\tau_N$ may be expressed as:

$$\tau_N = \tau_0 e^{\frac{KV}{kT}}$$

Where k is the Boltzmann constant, T the temperature and $\tau_0$ a constant. For large crystals the Nèel relaxation time is very long and magnetic moments are locked to the easy anisotropic axis. For crystals of less than 6 nm in diameter the transmissions are fast in the order of nanoseconds. When small ferrimagnetic crystals are in liquid media not only the Nèel relaxation time modulates the fluctuations but also the movement of the crystals. The Brownian or rotation time of the spin system is given by:

$$\tau_r = \frac{4\pi\alpha 3\eta}{3kT}$$

Where $\alpha$ is the radius of the particle and $\eta$ viscosity of the liquid. For a system of paramagnetic crystals the resulting magnetization is given by:

$$M = M_{sat} \cdot L(\alpha),$$

$$L(\alpha) = \coth(\alpha) - \frac{1}{\alpha},$$

$$\alpha = \mu \frac{B_0}{kT}$$

Wherein $B_0$ is the external magnetic field, $\mu$ is the total magnetic moment of the crystal and $M_{sat}$ defines the field at which the magnetization is locked or saturated along the low energy axis. Based in the discussion as described herein, superparamagnetic particles have magnetic moments much greater than the individual moments associated with the ions that make up the crystals and by the fact that in absence of an external field, the mean magnetic moment of the particles is zero due the average of the Nèel relaxation of crystals and rotation of the particles. Some principles of the invention are based in the fact that the distance between magnetic particles or crystals affects their magnetic behavior.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide matrices or compounds containing particles wherein the integrity of such matrices or compounds can be determined from the effect of the distribution of said particles on the measured magnetic properties.

In an additional preferred embodiment of this invention, the measurement of enzymatic activity can be carried out using magnetic particles coated with several proteins or carbohydrates which can be metabolized by a biological process and magnetically functionalized contrast agents can be prepared by aggregating those coated magnetic particles into a matrix that can be, without excluding other matrices, also made from collagen or other extracellular matrix components, thus the degradation of the matrix and/or the coating will cause the aggregation of the magnetic particles and therefore a measurable effect can be detected. In yet other preferred embodiment of the invention, magnetic particles can be attached to protein, carbohydrates, monomers or peptides and magnetically functionalized contrast agents can be prepared by aggregating those proteins, carbohydrates, monomers or peptides to conform a metabolizable matrix. In an example of this last embodiment, modified collagen is attached to magnetic particles to be used as reporter of MMP activity.

In a yet further embodiment of the invention, the immobilization of magnetic particles on substrates can be performed in vivo by means of providing magnetite nanoparticles coated with APTS, by means of first sonicating the particles in ethanol and then incubating them with APTS in ethanol for at least 8 h in a similar manner as described by H. Kobayashi et al, 1991. The ratio of ethanol/particles can be adjusted to determinate the coating degree. Thereafter, several ligands as macromolecules, proteins, amino acids, or their derivatives, can be anchored directly or indirectly as for example through an aldehyde linkage.

Some examples of such ligands can be denaturalized collagen and other gelatins, albumin, glycoproteins, etc. According to some embodiments of the present invention, macromolecules, such as gelatin are used as ligands. It is worthwhile to optimize the molecular size of such ligands For some in vivo applications of the invention, it will necessary achieve a size particles of 300 nm or less. For example, if gelatin is used as ligand gelatin fragments can be reduced in size by first partially digesting its precursor. Gelatin is produced by partial hydrolysis of denaturalized collagen. If before producing gelatin collagen is predigested first in monomers as described by F. S. Steven, 1967, then, when such modified magnetic particles are provided in dispersed suspensions to human or other living beings they can be immobilized on an extracellular matrix tissue. Thus, an enzymatic degradation of such extracellular matrix tissue will affect the distribution or state of aggregation of such particles, and therefore any they will be measurable changes in their magnetic properties. The extracellular matrix is composed by as plurality of fibrous proteins and glycosaminoglycans (GAGs). A complete reference of such fibrous proteins, its properties and functions can be found in the book "The Extracellular Matrix FactsBook" by Shirley Ayad et al. The cross linking of such extracellular matrix components is described by Kielty C M et al, 1993.

In one preferred embodiment of the invention, magnetic particles immobilized on extracellular matrix tissue can be spotted in a MRI measurement, or other measurement method, as a change in a magnetic parameter or relaxation time after a first baseline measurement and then once the location and or distribution of the immobilized particles is established, further measurements of magnetic parameters or relaxation times can provide an indication of degradation of extracellular matrix as a consequence of enzymatic activity.

The diagnosis of MMPs' activity merit consideration in catabolism of the extracellular matrix, which are related to unstable coronary disease.

The stability of atherosclerotic plaques is provided by extracellular matrix and a thick fibrous cap. Usually unstable plaque has a thin fibrous cap and thrombus at the shoulder, many inflammatory cells, and a large lipid core. The synthesis of collagen by smooth-muscle cells is stimulated by growth factors, such as transforming growth factor-β (TGF-β). Inflammation in plaques, with the accumulation of macrophages and T lymphocytes, leads to the release of MMPs, which digest collagen and cause thinning of the fibrous cap. The necrotic lipid core grows as a result of the accumulation of lipids in extracellular matrix, the death of lipid-laden macrophages, and perhaps the accumulation of erythrocyte membranes after intraplaque hemorrhage from the vasa vasorum.

Oxygen radicals, generated from many sources, including NADPH oxidase and inflammatory cells, oxidize low-density lipoproteins (LDL) and cause necrosis of cells. Repetitive cycles of plaque rupture and healing, which may be clinically silent, produce layers in the advanced plaque. In contrast to the intracellular proteolytic enzymes found in organelles called lysosomes, MMPs act extracellularly and at physiological pH. The matrix metalloproteinase superfamily includes interstitial collagenase, an enzyme specialized in the initial cleavage of the usually protease-resistant fibrillar collagens that confer strength upon the fibrous cap of the atheroma. Other matrix metalloproteinase family members (the gelatinases) catalyze further breakdown of collagen fragments. Stromelysins can activate other members of the matrix metalloproteinase family and can degrade a broad spectrum of matrix constituents, including the protein backbones of proteoglycan molecules. Stromelysin and one of the gelatinases (gelatinase B, or 92-kD gelatinase) can also break down elastin, an additional structurally important component of the vascular extracellular matrix.

Clinical evidence supported by molecular models shows that the risk of significant events in coronary disease, such as obstructions, stroke or acute myocardial infarction, are caused by plaque rupture due to MMPs induced by immunologic excretion of LDL, as previously described, but not by the size of obstructions. Therefore in another embodiment of the invention, a protein such as collagen, fibrillin, elastin, etc., without excluding other possible alternatives, can be used as active substrate as reporter to determinate the activity of MMPs in coronary plaque. In an embodiment of the invention, a magnetic contrast agent to assess collagenolytic activity of MMPs can be prepared by immobilizing superparamagnetic particles along residues on the hydrophilic surface of collagen fibrils, as for example lysine. Thus, when collagen is metabolized or digested such magnetic particles will tend to aggregate due to the interaction between magnetic moments which is the strongest intercolloidal interaction of the order of the inverse of the distance's cube. In preferred embodiments of the invention the labeling of collagen can be performed either in vitro, and therefore the modified collagen actuates as a smart contrast agent, or in vivo be means of modify endogenous collagen or other endogenous substrate or macromolecule as reporter of enzymatic activity.

There are several methods of attaching proteins to magnetic particles. One of them consists in coating them with a layer of aminosilane (APTS). This procedure produces magnetic nanoparticles with amino groups exposed at their surface that allow the particles to anchor peptidic residues that have free carboxyl groups. This method is based in the union of OH groups on the surface of ferrous oxide with the 3 $C_2H_5O-$ groups of the APTS leaving exposed to the environment adjacent to the amino group of the latter. OH groups are disposed over the surface of ferrous oxide particles at as a result of the absorption of H+ ions and OH— during their suspension in an aqueous medium.

The union between APTS and nanoparticles should take place in organic media for avoiding or minimizing the contact of APTS with water, so it is necessary to ensure the structural integrity of the proteins in these conditions. In an embodiment of the invention, this principle is used to coat ferrous oxide particles with APTS is applied as a method to immobilize ferrous oxide particles on collagen fragments or fibrils and thus achieve the aggregation of magnetic particles in the event that collagen will be digested.

A preferred method of measurement is MRI, wherein the aggregation or dispersion of magnetic particles can be measured as changes in the relaxation times and therefore in the contrast effect of such magnetic particles. In other preferred embodiments of the invention, collagen can be provided as either separated natural occurring or synthetic α chains and a similar process to immobilize magnetic particles can be carried out to some of those α chains or separated monomers thus some of these α chains can be induced to adopt a triple helix structure by suspending or dissolving them in, as example, an acidic medium and collecting the precipitates, washing, treating them with pepsin and filtering. FIG. 4 shows a scheme of a modified collagen tripeptide, A, functionalized with magnetite nanoparticles, B. The drawing is not in scale and the distribution of the magnetite nanoparticles does not necessary match a real distribution. FIG. 5 shows the effect of collagenolytic activity on the distribution of magnetic nanoparticles first immobilized on collagen after such collagen is digested by collagenases.

In another embodiment of the invention, magnetic particles already coated with APTS, dextran, starch or any other alternative anchoring layer can be attached or immobilized to collagen or any protein, lipoprotein, lipid or, in general, substrate of certain enzyme. There also exist additional methods to immobilize magnetic particles over proteins surface, as the using carbodiimide (CDI) in aqueous suspensions, falling all them in the scope of the invention. It is also contemplated by the invention that the substrate will coat the magnetic particles and to confine such coated particles within a matrix. An example of such matrix can be the agglomerate of the coated particles bounded by the coating substrate by itself. Thus under the effect of an enzyme this coating or matrix will be degraded releasing the magnetic particles which will tend to aggregate producing the measurable effects in magnetic contrast described above.

A preferred route of administration for this family of protein activate magnetic probes is, without excluding other existing or possible, intra venal preferably local. In yet another embodiment of the invention, MMPs sensible probes can encapsulate pharmaceutical agents to be release in the site of the target MMP activity.

It is also within the scope of the present invention to provide a method to diagnose an enzymatic or metabolic process by means of providing to an subject a contrast agent formulation containing magnetic particles immobilized either in vivo or in vitro on macromolecules or substrates and measuring changes in their magnetic properties or in the effects produced by such changes in their magnetic properties between a first a second time after providing such contrast agent formulation wherein such changes are a consequence of the change of the distribution of such magnetic particles.

It is additionally within the scope of the present invention to include such contrast agents in drug delivery formulation to assess the efficiency of such drug delivery composition.

In one preferred embodiment of the invention, superparamagnetic, paramagnetic or ferromagnetic particles can be bound or immobilized to a protein or macromolecule. The state of aggregation or proximity of such magnetic nanostructures or particles is possible to be measured by magnetic resonance imaging (MRI) or other imaging methods based in the measurement of magnetic properties or their effects.

Modern nuclear resonance methods, as for instance MRI or electron paramagnetic resonance (EPR), provide preferred indirect methods to measure such changes in magnetic properties. In such nuclear resonance methods are measured the relaxation times of response to the effect of applied RF perpendicular to a strong magnetic field. These relaxation times are called T1 and T2 and represent the characteristic times of the alienation of water protons as a consequence of the disappearance of a magnetic field at the longitudinal plane to the applied RF and the reappearance of the strength of the magnetic field at the perpendicular plane to the applied RF respectively as consequence of eliminating such RF. Compared to diamagnetic materials as most of the biological tissues and fluids are, T1 and T2 are significantly shorter in the presence of ferromagnetic, paramagnetic and superparamagnetic materials. It has long been recognized also that the addition of paramagnetic solutes to water causes a decrease in the measured T1 parameter of hydrogen protons of water.

MRI, as it is used in clinical applications, relies on the counterbalance between the exceedingly small magnetic moment on a proton, and the exceedingly large number of protons present in biological tissue, which leads to a measurable effect in the presence of large magnetic fields. Thus, even though the effect of a steady state field of $B_0=1$ T on a collection of protons, such as the hydrogen nuclei in a water molecule, is so small that it is equivalent to the moments of only three of every million proton being aligned parallel to $B_0$, there are so many protons available—6.6× $10^{19}$ n every $mm^3$ of water—that the effective signal, $2 \times 10^{14}$ proton moments per $mm^3$, is observable. This signal can be captured by making use of resonant absorption: applying a time-varying magnetic field in a plane perpendicular to B0, tuned to the Larmor precession frequency $\omega_0 = \gamma \beta_0$ of the protons. For $^1H$ protons the gyromagnetic ratio $\gamma = 2.67 \times 10^8$ $rad^{s-1} T^{-1}$, so that in a field of $B_0=1$ T the Larmor precession frequency corresponds to a radio frequency field with $\omega_0/2\pi = 42.57$ MHz. In practice the radio frequency transverse field is applied in a pulsed sequence, of duration sufficient to derive a coherent response from the net magnetic moment of the protons in the MRI scanner. From the instant that the radio frequency pulse is turned off the relaxation of the coherent response is measured via induced currents in pick-up coils in the scanner. These resonantly tuned detection coils enhance the signal usually by a quality factor of ca 50-100. For $B_0$ parallel to the z-axis these relaxation signals are of the form:

$$m_z = m(1 - e^{-t/T_1})$$

and $$m_{x,y} = m \sin(\omega_0 t + \varphi) e^{t/T_2}$$

wherein $T_1$ and $T_2$ are the longitudinal (or spin-lattice) and transverse (or spin-spin) relaxation times, respectively, and $\varphi$ is a phase constant. The longitudinal relaxation reflects a loss of energy, as heat, from the system to its surrounding lattice, and is primarily a measure of the bipolar coupling of the proton moments to their surroundings. The relaxation in the xy-plane is relatively rapid, and is driven by the loss of phase coherence in the processing protons due to their magnetic interactions with each other and with other fluctuating magnetic moments in the tissue. Dephasing can also be affected by local inhomogeneities in the applied longitudinal field, leading to the replacement of $T_2$ in second equation by the shorter relaxation time, $T^*_2$:

$$\frac{1}{T_2^*} = \frac{1}{T_2} + \gamma \frac{\Delta B_0}{2}$$

wherein $\Delta B_0$ is the variation in the field brought about either through distortions in the homogeneity of the applied field itself, or by local variations in the magnetic susceptibility of the system. This variation of $\Delta B_0$ can be precisely caused by magnetic particles with significant predominance over possible local factors of inhomogeneity of the field $B_0$. In some embodiments of the invention are the resulting differences in $\Delta B_0$ caused by changes in the distribution or aggregation state of magnetic particles that where first immobilized on substrates or other macromolecules of interest the cause of the signal detected as consequence of the degradation or metabolic use of such substrates or other macromolecules of interest.

It has to be noted that the effect of the alignment of the magnetic moments of magnetic particles can markedly vary as consequence of their grouping or distribution. It can be understood from two factors a) the effects of thermal or kinetic shaking, as was explained above, and b) the average time and energy needed to respond to an applied external magnetic field as it is explained below.

In another embodiment of the present invention, magnetic particles can be bound or immobilized in a matrix or complex molecule and the distribution or aggregation state of those magnetic particles varies as a consequence of a conformational transformation of such matrix or complex molecule. Said conformational transformation can be triggered by an enzymatic or metabolic process.

A special case of interest is wherein those magnetic particles are superparamagnetic and tend to aggregate as consequence of such conformational variation. Then the resulting magnetic aggregate is not necessarily superparamagnetic. Thus, its magnetic properties will be measurably different form those of the original magnetic particles. Therefore, by measuring the changes in the magnetic properties, a signal of an enzymatic or metabolic effect can be detected. In the case of magnetite nanoparticles, which are less than 14 nm in diameter, they are superparamagnetic when suspended in aqueous solutions at biological temperatures, but became paramagnetic if they aggregate in clusters of more than 14 nm of diameter.

Figure 1:
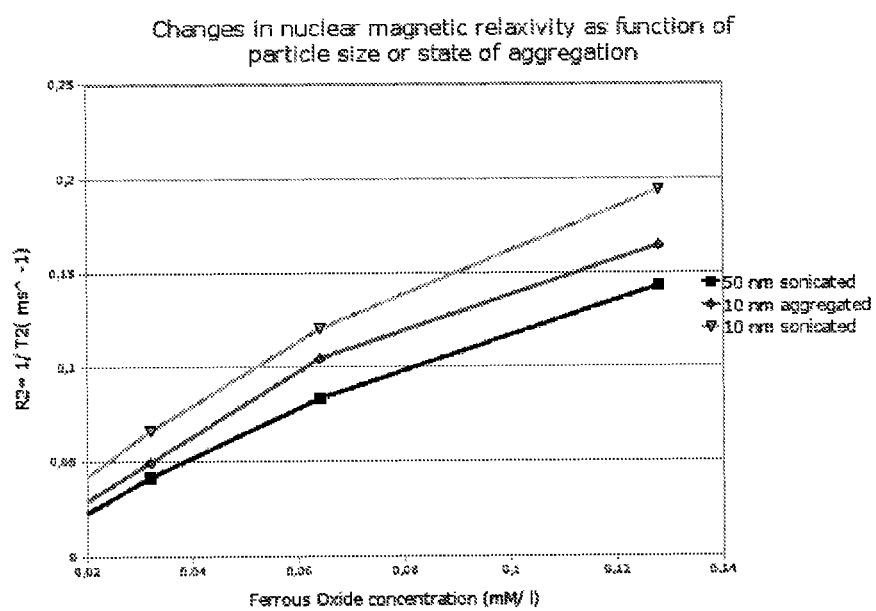

FIG. 1 shows the effect of the size and the aggregation of magnetite superparamagnetic and paramagnetic nanoparticles on the measurement of the inverse of $T_2$ also called magnetic relativity $R_2$. It can be observed that once aggregated superparamagnetic nanoparticles behaves more as paramagnetic particles.

If a magnetic material is placed in a magnetic field of strength H, the individual atomic moments in the material contribute to its overall response, the magnetic induction:

$$B = \mu_0 (H + M)$$

where $\mu_0$ is the permeability of free space, and the magnetization $M = m/V$ is the magnetic moment per unit volume, where m is the magnetic moment on a volume V of the material. All materials are magnetic to some extent, with their response depending on their atomic structure and temperature. They may be conveniently classified in terms of their volumetric magnetic susceptibility, $\chi$, where $M = \chi H$ describes the magnetization induced in a material by H. In SI units $\chi$ is dimensionless and both M and H are expressed in $Am^{-1}$.

The susceptibility in ordered materials depends not just on temperature, but also on H, which gives rise to the characteristic sigmoidal shape of the M-H curve, with M approaching a saturation value at large values of H. Furthermore, in ferromagnetic and ferrimagnetic materials it is often seemed hysteresis, which is an irreversibility in the magnetization process, that is related to the spinning of magnetic domain walls at impurities or grain boundaries within the material, as well as to intrinsic effects such as the magnetic anisotropy of the crystalline lattice. This gives rise to open M-H curves, called hysteresis loops. The shape of these loops are determined in part by particle size: in large particles (of the order of micron size or more) there is a multi-domain ground state which leads to a narrow hysteresis loop since it takes relatively little field energy to make the domain walls move;

while in some smaller particles there is a single domain ground state which leads to a broad hysteresis loop. At even smaller sizes (of the order of tens of nanometers or less) one can see superparamagnetism, where the magnetic moment of the particle as a whole is free to fluctuate in response to thermal energy, while the individual atomic moments maintain their ordered state relative to each other. This leads to an anhysteretic, but still sigmoidal, M-H curve. Even for superparamagnetic particles when disposed in bulk their magnetic moments will interact affecting M-H curves (even hysteresis can be observed in some cases) and relaxation times and resulting in other magnetic and optical effects.

Figure 2:
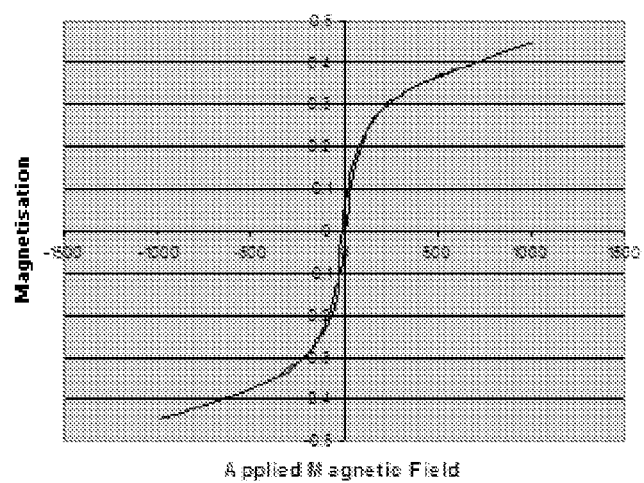

This effect can be appreciated measured by magnetic vibrational spectrometry (MVS) in the following graphs. FIG. 2 represents the M-H curve of type IV collagen functionalized with superparamagnetic magnetite nanoparticles with a diameter of 10 nm in 10 ml of saline suspension immobilized in agarose.

Figure 3:
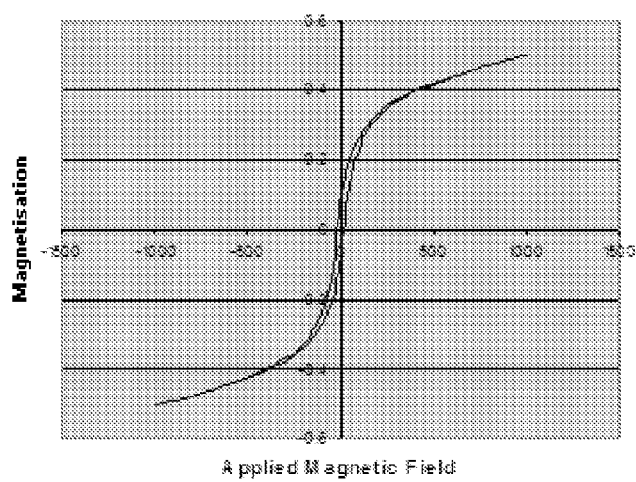

FIG. 3 represents the H-M curve of a similar suspension immobilized in agarose after incubation with type I collagenase for 12 h at 37° C. In FIG. 3, a slightly open curve can be appreciated, however the H-M curve of FIG. 2 is totally anhysteretic. This magnetic behavior results from the interaction between magnetic moments of the nanoparticles after they aggregate as consequence of the collagenolytic activity of the collagenase. When collagenase hydrolyzes collagen, separated alpha chains are released and the anchored magnetic nanoparticles tend to aggregate as a consequence of thermal motion inducing magnetic coupling between the magnetic domains of the aggregated magnetic nanoparticles.

There also exist several methods to measure and/or determinate the magnetic properties and/or the alignment and/or distribution of the magnetic moments of materials that can be utilized to carrying out the invention. These methods include, without exclude other existing or future methods, MVS, gamma, X resonance or Mössbauer spectrometry, EPR, MNR, electromagnetic inductance, atomic force microscopy, magnetorelaxometry etc.

In other embodiment of the invention magnetic particles already coated with APTS, dextran, starch or any other alternative anchoring layer can be attached or immobilized to collagen or any protein, lipoprotein, lipid or, in general, substrate of certain enzyme.

There also exist additional methods to immobilize magnetic particles over proteins surface, employing carbodiimide (CDI) in aqueous suspensions, which also falls within the scope of the invention.

It is also contemplated by the invention that the substrate will coat the magnetic particles and to confine such coated particles within a matrix. An example of such matrix can be the agglomerate of the coated particles bounded by the self coating substrate. Thus under the effect of an enzyme this coating or matrix will be degraded releasing the magnetic particles which will tend to aggregate producing the measurable effects in magnetic contrast described above.

One preferred route of administration for this family of protein activate magnetic probes is, without excluding other existing or possible, intra-venal, preferably local. A detailed list of possibilities for the delivery of the formulation is provided by John M. Walker at the book Macromolecular drug delivery: methods and protocols.

In yet another embodiment of the invention, MMPs sensible probes can encapsulate pharmaceutical agents to be release in the site of the target MMP activity.

MMPs are also highly related to liver disease. Liver fibrosis and cirrhosis involve multiple cellular and molecular events that lead to deposition of an excess of extracellular matrix proteins and increase the distortion of normal liver architecture. Etiologies include chronic viral hepatitis, alcohol abuse fatty liver, non alcoholic steatosis and drug toxicity. Over expression of MMPs is one of the molecular markers that can differentiate liver steatosis from fibrosis or cirrhosis. Furthermore a type of collagenase (MMP-13) and other MMPs have an transient increased activity in the early stage of hepatic fibrosis and a reduced activity in advanced fibrosis.

A progressive net disposition of type I and III collagens has been observed during the progress of fibrosis. Other MMPs than MMP-1, MMP-8 and MMP-13 cannot cleave type I collagen. MMP-2, MMP-3 and MMP-9 can clave type IV collagen and the enzymatic activity of these MMPs progressively decreases with the onset of cirrhosis. Molecular studies of the expression of mRNA for these enzymes (including those with collagenolytic activity) have shown that they are expressed in the liver even in cirrhosis, but their activity is held in check by powerful inhibitors, the tissue inhibitors of metalloproteinases (TIMPs) 1 and 2. The potential for matrix degradation is present, even in advanced cirrhosis—but it is held in check by concurrently secreted TIMPs.

It is believed that regression of liver fibrosis is mediated by decreased expression of TIMPs and involves degradation of fibrillar collagens by a combination of MT1-MMP and gelatinase A, in addition to interstitial collagenase. It should be possible to unharness the latent matrix degrading capacity of a fibrotic or cirrhotic liver and to facilitate matrix degradation, resulting in a return to normal or near normal architecture. Kupffer cells as well as lipocytes cells play a central role in synthesis of MMPs and TIMPs. In general, nano- and micro-particles are markedly retained by Kupffer cells at the liver.

When the magnetic particles immobilized on collagen, as described above are administered or delivered to the liver, compared to normal liver, at the end stages of steatosis or hepatosteatosis and beginning of fibrosis an enhanced contrast effect will be observed by methods as MRI, but a more moderated contrast effect is observed during later stages of fibrosis or cirrhosis. It is understood that such results may be affected by dose, protocols of preparation or administration and instruments of measurement without affecting the validity of the method. Furthermore these or other variations of the method are included within the scope of the present invention.

Administering magnetically functionalized collagen as described above, is useful to assess hepatic conditions by determining MMPs collagenolytic activity in the liver. The resulting probes have a contrast effect characterized by significantly different relaxation times for those water protons which are close to the magnetic particles anchored to collagen. This effect in relaxation is even enhanced if magnetic particles aggregate as consequence of MMPs activity.

Thus the grade of such enhanced contrast effect on MRI image is a signal of MMPs expression. This enhancement in contrast effect of the magnetic resonance signal can be measured over the time by different parameters utilized in magnetic resonance imaging measurements such as the signal strength, T1 or T2 weighted images, calculation of diffusion parameters, saturation images or a combination thereof without excluding other NMR parameters not enumerated in this application. A short description of some of those parameters is provided as follows.

The basic parameters of image acquisition in MRI are called the echo time (TE) and the repetition time (TR) with are the time in milliseconds between the application of a RF pulse able to flip on 90° the magnetic moment or spin of water protons (90° pulse) and the amount of time that exists between successive RF pulse sequences applied to the same sample slice respectively. A spin echo pulse is an RF pulse sequence type that usually employs a 90° pulse, followed by one or more 180° pulses. A T2 weighted image is the image made with a sequence with long TR and TE to show contrast in tissues with varying T2 relaxation times; water gives a strong signal. In the other hand, T1 weighted images MRI made with pulse spin echo or inversion recovery sequence with short TR and TE to show contrast between tissues with different T1 values. T*2 (pronounced "T 2 star") weighted scans use a spacial gradient echo (GRE) pulse sequence, with long TR and long TR. The gradient echo sequence used does not have the extra refocusing pulse used in spin echo so it is subject to additional losses above the normal T2 decay (referred to as T2'), these taken together are called T*.

Diffusion MRI measures the diffusion of water molecules in biological tissues. In an isotropic medium inside a glass of water, for example, water molecules naturally move randomly according to turbulence and Brownian motion. In biological tissues however, where the Reynold's number is low enough for flows to be laminar, the diffusion may be anisotropic. In diffusion weighted imaging (DWI), each image voxel (three dimensional pixel) has an image intensity that reflects a single best measurement of the rate of water diffusion at that location. Saturation MRI made with very shorts TR and TE. A more complete description of MRI parameters and principles is provided by D. G. Mitchell et al in the book "MRI Principles".

In another embodiment of the present invention, compared to normal liver, at the end stages of steatosis or hepatosteatosis and beginning of fibrosis faster appearance of enhanced contrast effects will be observed by methods as MRI, but a more moderated contrast effect is observed during later stages of fibrosis or cirrhosis.

It is understood that such results may be affected by dose, protocols of preparation or administration and instruments of measurement without affecting the validity of the method. Furthermore these or other variations of the method are included within the scope of the invention.

MMP expression is also significantly higher in patients with hepatic metastases. In cancer, the balance between production and activation of MMPs and their inhibition by TIMPs is a crucial aspect of cancer invasion and metastasis. MMPs synthesized in tissues seep into the bloodstream and it was observed that in colorectal, breast, prostate, and bladder cancer, most patients with aggressive disease have increased plasma levels of gelatinase B.

In patients with advanced colorectal cancer, high levels of either gelatinase B or TIMP complex were associated with shortened survival. Thus, it is within the scope of the invention to use the principle of change on distribution of magnetic particles initially immobilized on substrates, macromolecules or matrices to assess the activity of MMPs or other enzymes in organs or extra organic tissues and body compartments.

EXAMPLES

Some possible and preferred embodiments for carrying out the invention are described below. These examples are only some of the many alternatives that can be derived from the above summary of the invention.

Example 1—Preparation of a Magnetized Collagen Modified Substrate

Commercial type I collagen from bovine tendon has a triple helix structure and proven collagenolytic substrate properties. The selection of fragments of collagen with a triple helical structure is done through a treatment with pepsin and subsequent filtering. This process can be ensured by circular dichroism.

To join the aminosilane (APTS) to collagen's lysines, the latter is activated with glutaric anhydride to conform a complex. This reaction is carried out using N, N-Diisopropylethylamine (DIEA). Thus APTS, glutaric anhydride and DIEA in a 1:1:3 ratio, are dissolved in chloroform and mixed for 24 h in a dry atmosphere. The modified APTS. Magnetic particles of less than 15 nm of diameter suspended in a usually acid aqueous medium are mixed in ethanol in an ethanol/water ratio of at least 98:1 and sonicated.

The magnetic particles are resuspended in further ethanol, added to the mixture containing the activated APTS and it is mixed for 8 hours and chloroform is removed by evaporation with nitrogen. A suspension of collagen in ethanol with diisopropil carbodiimide (DIPCD) in a 1:1 respect to the quantity of lysines estimated from collagen's composition and mixing for 48 hours. The resulting suspension is washed with further ethanol, resuspended in water and collagen fibrils modified with immobilized magnetic particles are separated from excesses by means of is consecutively washed with ethanol and resuspended in deionized water.

Excesses are eliminated through columns, gradient centrifugation or magnetic separation, dialyzed and are lyophilized. The resulting formulation is useful for the detection of collagenolytic activity in vivo, in vitro or ex vivo. Due to collagen triple helix structure, once collagen is degraded by an enzyme the attached magnetic particles will tend to be aggregated or dispersed according their original distribution along the collagen's chains. This change of the distribution of magnetic particles can be measured by some of the methods of magnetic measurements described at the present application, however other methods can be applied without departing from the spirit and scope thereof.

Example 2—Assessment of Collagenolytic, Activity in the Liver 200 mg of collagen fibrils of 300 nm length functionalized with superparamagnetic particles are prepared with some of the methods described above and prepared for human or animal administration for either oral administration by means of encapsulate the modified collagen fibers or for intra venal administration through a catheter to the portal vein then a serial of MRI scans of the liver are performed and T2 weighted images are obtained after a T2 weighted image as baseline.

Depending in the mode of collagen administration, most of the collagen must reach the liver in a timer lower than 1 hour after obtaining in this time an steady state T2 weighted image of the liver and stored as time A. T2 values of time A image will be significantly shorter at the proximity of the magnetically functionalized collagen. Additional T2 weighted images of the liver are performed hours afterward and stored. T2 values of the T2 weighted images are averaged after eliminating possible artifacts and physiological noises as, for example, bloodstream or hollow cavities.

Thus if the averaged T2 values of the images obtained after time A are significantly lower than the average T2 value obtained at time A then there is a signal of collagenolytic activity in the liver.

In another embodiment of the invention a similar procedure is performed but a baseline MRI scan is measured prior to the magnetically functionalized collagen fibrils administration. Results can be more accurate if they are only observed the regions where the modified collagen fibrils are located. Preliminary results shows that a reduction of a 10% at the measured T2 values in T2 weighted images of 5 mg of injected collagen functionalized with superparamagnetic particles will be a signal of collagenase activity.

Example 3—Diagnosing Connective Tissue Regeneration in Dupuytren's Disease

A formulation composed of 0.05 mM of superparamagnetic nanoparticles modified with immobilized gelatin, prepared from predigested collagen, and suspended in saline serum are administered by intravenous injection between the affected fingers of a patient who suffers of Dupuytren's Disease and T2 weighted images are obtained after a T2 weighted image as baseline. T2 values of time A image will be significantly shorter at the proximity of the modified nanoparticles immobilized to endogenous patient extracellular matrix of the connective tissue through gelatin linking.

Additional T2 weighted images of the affected hand are performed hours afterward and stored. T2 values of the T2 weighted images are averaged after eliminating possible artifacts and physiological noises as, for example, bloodstream, burbles or hollow cavities. Thus if the averaged T2 values of the images obtained after time A are significantly lower than the average T2 value obtained at time A then there is a signal of MMP activity related to connective tissue regeneration. A lack of MMP activity will be an enzymatic cause of Dupuytren's Disease.

It can be understood from the above examples, that there are many methods for diagnosing an enzymatic activity in a living organism within the scope of the present invention. The methods generally comprise combining at least one magnetic particle to a substrate to form a modified substrate, providing the modified substrate to a living organism, performing a measurement related to the magnetization of the modified substrate thereby diagnosing a metabolic or enzymatic activity occurring in said living organism.

The measurement may be performed by a method such as magnetic resonance imaging (MRI) or other methods known in the art. According to some embodiments, the substrate is collagen.

The present invention may be embodied in other specific forms without departing from the spirit and scope thereof. These and other modifications of the invention will occur to those skilled in the art. Such other embodiments and modifications are intended to fall within the scope of the invention.

The term "fine matrix" refers hereinafter to any micro or nano-sized matrix or composition, and especially to a matrix o composition ranging from 1 nanometer to 5 centimeters, more particularly a probe or matrix or a plurality of probes or matrices ranging from 5 nanometers to 5 micrometers. The term "fine matrix" includes as well the possibility of provide such probes or matrices in the any of forms of colloidal suspension, solution or encapsulated.

It is within the scope of the present invention to provide a method to diagnose a biological process by mean of administering to an human or lower animal a fine matrix characterized by magnetic properties, wherein said fine matrix is adapted to alter its magnetic properties in care of its degradation.

It is within the scope of the present invention to provide a method to diagnose a biological process by mean of administering to a human or lower animal a fine matrix composed by at least one diamagnetic and a plurality of non diamagnetic elements, wherein said non diamagnetic elements tend to aggregate matrix in care of the fine matrix degradation.

It is also within the scope of the present invention to provide a method to diagnose a biological process by mean of administering to an human or lower animal the fine matrix as described herein wherein such non diamagnetic elements are coupled to such at least one diamagnetic element in vivo.

It is also within the scope of the present invention to provide a method to diagnose a biological process by mean of administering to an human or lower animal the fine matrix as described herein wherein the degradation of said fine matrix is observable by a sequential or continuous series of images during a single image procedure by a magnetic resonance or magnetic resonance imaging system.

It is further within the scope of the present invention to provide a method to diagnose a biological process as described herein wherein the rate of change of the magnetic properties of said degradable fine matrix are a signal of one parameter selected form the group of stability, solubility, integrity or a combination thereof of said fine matrix.

It is further within the scope of the present invention to provide a method to diagnose a biological process as described herein wherein one of the fine probes as described herein is bounded in a drug compound or matrix.

It is further within the scope of the present invention to provide a method for measuring the change of a parameter of a compound or matrix selected form the group of stability, solubility, integrity or a combination thereof by means of binding one of the fine matrices as described herein and measuring the magnetic properties of said fine matrix or the products of its dissolution.

It is further within the scope of the present invention to provide a method for detecting a biological process as described herein wherein said fine probe is bounded in said compound or matrix under the effect of an external magnetic field.

It is further within the scope of the present invention to provide a method for diagnose a biological process as described herein wherein said external magnetic field is constant.

It is further within the scope of the present invention to provide a method for diagnose a biological process as described herein wherein said external magnetic field is variable in time.

It is further within the scope of the present invention to provide a method for detecting a biological process as described herein wherein said external magnetic field is heterogeneous.

It is further within the scope of the present invention to provide a method for detecting a biological process as described herein wherein the magnetic properties of said compound or matrix are measured by electromagnetic inductance.

It is further within the scope of the present invention to provide a method for detecting a biological process as described herein wherein the magnetic properties of said compound or matrix are determined by measuring the optical properties of said formulation or said dissolved products.

It is further within the scope of the present invention to provide a method for detecting a biological process as described herein wherein said optical properties are selected from the group of absorption, refraction, scattering, polarization, resonance or a combination thereof.

It is further within the scope of the present invention to provide a method for detecting a biological process as described herein wherein the magnetic properties of said compound or matrix are measured by nuclear magnetic resonance or magnetic resonance imaging.

It is further within the scope of the present invention, to provide a method for detecting a biological process as described herein wherein the magnetic properties of said fine matrix fine matrix are measured by electromagnetic inductance.

It is further within the scope of the present invention, to provide a method for detecting a biological process as described herein wherein the magnetic properties of said fine matrix are determined by measuring the optical properties of said formulation or said dissolved products.

It is further within the scope of the present invention to provide a method for detecting a biological process as described herein wherein said optical properties are selected from the group of absorption, refraction, scattering, polarization, resonance or a combination thereof.

It is further within the scope of the present invention to provide a method for diagnosing or detecting a biological process as described herein wherein the magnetic properties of said fine matrix are measured by nuclear magnetic resonance or magnetic resonance imaging.

The term "magnetic matrix-containing fine probe" hereinafter refers to any micro- or nano-sized probe, capsule or matrix comprising any of the fine matrices from above, and especially to a probe, capsule or matrix, comprising any of the fine matrices from above, ranging from 1 nm to 5 micrometers, more particularly a probe or matrix, comprising any of the fine matrices from above, ranging from 5 nm to 1 micrometers.

It is also within the scope of the present invention to provide a method to detect or diagnose a biological process by mean of administering to an human or lower animal a magnetic matrix containing—fine probe comprising a first element or matrix and a first and second magnetic element wherein a change in the placement of said first and second magnetic elements are a signal of a conformational change or degradation of said first element or matrix.

It is also within the scope of the present invention to provide a method to diagnose or detect a biological process as described herein wherein said biological process is an indication of the activity of an enzyme.

It is also within the scope of the present invention to provide a method to diagnose or detect a biological process as described herein wherein said enzyme is a lipase or protease.

It is also within the scope of the present invention to provide a method for diagnosing or detecting a biological process as described herein wherein said lipase or protease is one of a lipoprotein lipase, hormone sensitive lipase or matrix metalloproteinases.

It is also within the scope of the present invention to provide a method for diagnosing or detecting a biological process as described herein wherein said biological process is an indication of a metabolic, inflammatory or infection condition.

It is also within the scope of the present invention to provide a method for diagnosing or detecting a biological process as described herein wherein said biological process is an indication of tissue regeneration, cancer, coronary or liver disease.

It is also within the scope of the present invention to provide a method for diagnosing or detecting a biological process as described herein wherein said liver disease is related to one of the conditions of the group of metastasis, steatosis, hepatosteatosis, fibrosis or cirrhosis.

It is also within the scope of the present invention to provide a method for diagnosing or detecting a biological process as described herein wherein said indication of a predetermined biological process can differentiate between steatosis, fibrosis or cirrhosis.

It is also within the scope of the present invention to provide a method for diagnosing or detecting a biological process as described herein wherein said coronary disease is an indication of the location or severity of unstable plaque.

It is also within the scope of the present invention to provide a method for diagnosing or detecting a biological process as described herein wherein said indication of tissue regeneration is related to rheumatitis, arthritis, injuries or Dupuytren's or Peyronie's diseases.

It is also within the scope of the present invention to provide a method for diagnosing or detecting a biological process by means of administering to an human or lower animal a fine probe comprising in its components one diamagnetic compound and at least two non-diamagnetic particles wherein the disruption of the integrity of said fine probe is induced by the metabolic utilization or biological degradation of said diamagnetic compound by an enzyme of the list of lipoprotein lipase, hormone sensitive lipase or matrix metalloproteinases and said metabolic utilization or biological degradation of said diamagnetic compound causes a measurable aggregation of said at least two non-diamagnetic particles.

It is also within the scope of the present invention to provide a method for diagnosing or detecting a biological process by means of administering to a human or lower animal a plurality of the fines probes as described herein in colloidal suspension or encapsulated.

It is also within the scope of the present invention to provide a method for diagnosing or detecting a biologic process as described herein, wherein such aggregation of said at least two non-diamagnetic particles is measured either by nuclear magnetic resonance, magnetic resonance imaging, electronic paramagnetic resonance, magnetometry, Mössbauer spectrometry, electromagnetic inductance, atomic force microscopy, magnetorelaxometry or a combination thereof.

It is also within the scope of the present invention to provide a method for diagnosing or detecting a biological process as described herein, wherein such measurement with magnetic resonance imaging detects at least one of the parameters of the group of signal intensity, T1, T2, diffusion and a response to a saturation signal.

It is also within the scope of the present invention to provide a method to diagnose a biologic process as described herein wherein the metabolic utilization or biological degradation of said compound by an enzyme of the list of lipoprotein lipase, hormone sensitive lipase or matrix metalloproteinases induces the release of a therapeutic agent.

It is also within the scope of the present invention to provide a method to diagnose a biological process as described herein wherein such therapeutic agent is intended to treat cancer, coronary or liver disease.

It is also within the scope of the present invention to provide a method to diagnose a biological process as described herein wherein such therapeutic agent is intended to treat a genetic disease.

It is also within the scope of the present invention to provide a method to diagnose a biological process by means of administering to a human or lower animal a magnetic contrast agent in which an enhancement in its contrast effect is an indication of a predetermined biological process.

It is also within the scope of the present invention to provide a method to diagnose a biological process as described herein wherein said diamagnetic compound is a protein.

It is also within the scope of the present invention to provide a method to diagnose a biological process as described herein wherein said metabolic utilization of said compound produces a variation on the primary, secondary, tertiary or quaternary structure molecular structure of said compound.

It is also within the scope of the present invention to provide a method to diagnose a biological process as described herein wherein said biological predetermined process is the activity of an enzyme.

It is also within the scope of the present invention to provide a method to diagnose a biological process as described herein wherein said enzyme is a lipase or protease.

It is also within the scope of the present invention to provide a method to diagnose a biological process as described herein wherein said lipase or protease is one of the list of lipoprotein lipase, hormone sensitive lipase or matrix metalloproteinases.

It is also within the scope of the present invention to provide a method to diagnose a biological process as described herein wherein said biological process is an indication of a metabolic, inflammatory or infection condition.

It is also within the scope of the present invention to provide a method to diagnose a biological process as described herein wherein said biological process is an indication of a disease or disorder.

It is also within the scope of the present invention to provide a method to diagnose a biological process as described herein wherein said biological process is an indication of tissue regeneration, cancer, coronary or liver disease.

It is also within the scope of the present invention to provide a method to diagnose a biological process as described herein wherein said liver disease is an indication of one of the conditions of the group of metastasis, steatosis, hepatosteatosis, fibrosis or cirrhosis.

It is also within the scope of the present invention to provide a method to diagnose a biological process as described herein wherein said coronary disease is an indication of the location or severity of unstable plaque.

It is also within the scope of the present invention to provide a method to diagnose a biological process as described herein wherein said indication of tissue regeneration is related to rheumatitis, arthritis, injuries or Dupuytren's or Peyronie's diseases.

It is also within the scope of the present invention to provide a method to diagnose a biological process as described herein wherein said biological process can differentiate between steatosis, fibrosis or cirrhosis.

It is also within the scope of the present invention to provide a method to diagnose a biological process as described herein wherein such fine probe or matrix is a drug delivery system.

It is further within the scope of the present invention to provide a method of determining a predetermined biological process by providing to an human or lower animal any of the magnetic matrix containing a fine probe as described herein, the contrast agent as described herein or the colloidal suspension as described herein and measuring local changes produced by the magnetic characteristics of said magnetic matrix containing a fine probe, the contrast agent or the colloidal suspension.

It is further within the scope of the present invention to provide a method of determining a predetermined biological process by incubating a sample with any of the magnetic matrix containing a fine probe as described herein, the contrast agent as described herein or the colloidal suspension as described herein and measuring local changes produced by the magnetic characteristics of said magnetic matrix containing a fine probe, the contrast agent or the colloidal suspension.

It is further within the scope of the present invention to provide the method of determining a predetermined biological process by incubating a sample as described herein wherein said sample is an organic sample.

It is further within the scope of the present invention to provide a method of determining a predetermined biological process by incubating a sample as described herein wherein said an organic sample is a living tissue.

It is further within the scope of the present invention to provide a method of determining a predetermined biological process by incubating a sample as described herein wherein said an organic sample is an extracted tissue, fluid or excretion.

It is further within the scope of the present invention to provide a method of determining a predetermined biological process by incubating a sample as described herein wherein said biological predetermined process is the activity of an enzyme.

It is further within the scope of the present invention to provide the method of determining a predetermined biological process by incubating a sample as described herein wherein said enzyme is a lipase or protease.

It is further within the scope of the present invention to provide the method of determining a predetermined biological process by incubating a sample as described herein wherein said lipase or protease is one of a lipoprotein lipase, a hormone sensitive lipase and a matrix metalloproteinases.

It is further within the scope of the present invention to provide the method of determining a predetermined biological process by incubating a sample as described herein wherein said biological process is an indication of a metabolic, inflammatory or infection condition.

It is further within the scope of the present invention to provide the method of determining a predetermined biological process by incubating a sample as described herein wherein said biological process is an indication of a disease or disorder.

It is further within the scope of the present invention to provide the method of determining a predetermined biological process by incubating a sample as described herein wherein said biological process is an indication of tissue regeneration, cancer, coronary or liver disease.

It is further within the scope of the present invention to provide the method of determining a predetermined biological process by incubating a sample as described herein wherein said liver disease is an indication of one of the conditions of the group of metastasis, steatosis, hepatosteatosis, fibrosis or cirrhosis.

It is further within the scope of the present invention to provide the method of determining a predetermined biological process by incubating a sample as described herein wherein said indication of a predetermined biological process can differentiate between steatosis, fibrosis or cirrhosis.

It is further within the scope of the present invention to provide the method of determining a predetermined biological process by incubating a sample as described herein wherein said coronary disease is an indication of the location or severity of unstable plaque.

It is yet within the scope of the present invention to provide the method of determining a predetermined biological process by incubating a sample as described herein wherein said indication of tissue regeneration is related to rheumatitis, arthritis, injures or Dupuytren's or Peyronie's diseases.

It is also within the scope of the present invention to provide the method of determining a predetermined biological process as described herein wherein said local changes are a consequence of changes in the stability or conformation of said magnetic matrix containing a fine probe, the contrast agent or the colloidal suspension.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as herein before described without departing from its scope, defined in and by the appended claims.

REFERENCES

1. Woessner J F Jr., in Matrix metalloproteinases and their inhibitors in connective tissue remodeling, FASEB J. 1991 May; 5(8):2145-54 and by Somers K D, Dawson DM in Fibrin deposition in Peyronie's disease plaque J. Urol. 1997 January; 157(1):311-5.
2. Kobayashi and T. Matsunaga in Amino-silane modified superparamagnetic particles with surface-immobilized enzyme, Journal of Colloid and Interface Science Volume 141, Issue 2, February 1991, Pages 505-511.
3. F. S. Steven in Single-stage partial depolymerisation of collagen fibrils, Biochimica et Biophysica Acta, 1967, 130, vol. 1, pages 196-201, the will be result in smaller gelatin fragment.
4. The Extracellular Matrix Facts Book, Shirley Ayad, Ray Boot-Handford, Martin J. Humphries, Karl E. Kadler and Adrian Shuttleworth ISBN: 978-0-12-068911-8.
5. Kielty C M, Hopkinson I and Grant M E, Collagen. The Collagen Family: Structure, assembly, and organization in the extracellular matrix. In Royce P M & Steinmann B (ed) Connective Tissue and 1st Heritable Disorders. Molecular, Genetics, and Medical Aspects. Wiley-Liss, Inc., New York. pp. 103-147.
6. John M. Walker, Macromolecular drug delivery: methods and protocols, Volume 480 from Methods in molecular biology, Springer protocols.
7. Donald G. Mitchell, Mark Cohen, Mark Cohen (Ph.D.), MRI principles, Saunders, 2004, ISBN 0.721600247, 9780721600246.

What is claimed is:

1. A method for detecting activity of an enzyme in a sample, consisting of the steps in order:
   (1) selecting at least one macromolecule, wherein at least one of the at least one macromolecule is selected from the group consisting of a protein, a polypeptide, a modified protein, a modified polypeptide, a glycoprotein, a lipoprotein, collagen, one or more collagen fragments, a mixture of collagen with one or more collagen fragments, and gelatin;
   (2) measuring and detecting the sample's magnetic property for a baseline measurement;
   (3)(A) (i) creating a substrate, the substrate is a plurality of magnetic particles covalently bound, by means of a process that involves silanization, to the at least one macromolecule;
   (ii) measuring and detecting a magnetic property of the substrate to obtain a first measurement;
   (iii) incorporating the substrate in the sample; or
   (3)(B) (i) creating a substrate in the sample, the substrate is a plurality of magnetic particles covalently bound, by means of a process that involves silanization, to the at least one macromolecule;
   (ii) measuring and detecting a magnetic property of the sample to obtain a first measurement;
   (4) measuring and detecting, after obtaining the first measurement, the magnetic property of the sample to obtain a second measurement;
   (5) comparing the first measurement to the second measurement; and
   (6) determining the substrate was degraded by the enzyme and detecting enzymatic activity if there is a change between the first measurement and the second measurement;
   wherein said change is indicative of at least one of (a) aggregation of said plurality of magnetic particles, (b) dispersion of said plurality of magnetic particles, (c) a change in the size of said plurality of magnetic particles, and (d) a change in the size of said substrate.

2. The method of claim 1, wherein the baseline measurement and the first measurement are the same.

3. The method of claim 1, wherein the first measurement and the second measurement are the same.

4. The method of claim 1, wherein the plurality of magnetic particles are selected from the group consisting of (a) magnetic nanoparticles, (b) superparamagnetic particles and (c) paramagnetic particles.

5. The method of claim 4, wherein the sample is an in vitro sample.

6. The method of claim 4, wherein the sample is an in vivo sample which is present in a subject.

7. The method of claim 6, wherein the enzymatic activity is indicative of a disease or condition.

8. The method of claim 7, wherein said disease or condition is selected from the group consisting of rheumatitis, arthritis, an injury, connective tissue condition related disease, Dupuytren's disease, Peyronie's disease, a collagen related disease, steatosis, fibrosis, cirrhosis, metastasis, tissue regeneration, cancer, coronary disease, a liver disease, a metabolic condition, an infection and an inflammatory disease.

9. The method of claim 1, wherein creating the substrate of step (3)(B) is effected in situ in said sample.

10. The method of claim 1, wherein creating the substrate of step (3)(A) is effected ex situ not in said sample.

11. The method of claim 1, wherein the enzyme is selected from the group consisting of a metal-dependent enzyme, a protease, a lipase, a lipoprotein lipase, a hormone sensitive lipase, a metalloprotease, a matrix metallo-proteinase (MMP), a collagenase and a gelatinase.

12. The method of claim 1, wherein the magnetic property is detected by a method selected from the group consisting of nuclear magnetic resonance (NMR), magnetic resonance imaging (MRI), electronic paramagnetic resonance (EPR), magnetometry, Mössbauer spectrometry, electromagnetic inductance, atomic force microscopy, magnetorelaxometry and a combination thereof.

13. The method of claim 1, wherein said magnetic property is measured indirectly by measuring at least one of a member of the group consisting of a signal intensity, T1 relaxation, T2 relaxation, a diffusion parameter and a response to a signal saturation.

14. The method of claim 13, wherein said determining includes determining if a change in said magnetic property has been observed.

15. The method of claim 14, wherein said change in said magnetic property is an at least partial change from superparamagnetism to paramagnetism.

16. The method of claim 1, wherein said aggregation or said change in the size of said plurality of magnetic particles is a consequence of magnetic attraction between magnetic particles.

17. The method of claim 1, wherein the at least one macromolecule is a first at least one macromolecule combined to a second at least one macromolecule.

18. The method of claim 17 wherein the first macromolecule is covalently bound to the plurality of magnetic particles.

19. A method for detecting the integrity of a substrate for an enzyme, consisting of the steps in order:
selecting at least one macromolecule, wherein at least one of the at least one macromolecule is selected from the group consisting of a protein, a polypeptide, a modified protein, a modified polypeptide, a glycoprotein, a lipoprotein, collagen, one or more collagen fragments, a mixture of collagen with one or more collagen fragments, and gelatin;
creating the substrate, the substrate is a plurality of magnetic particles covalently bound, by means of a process that involves silanization, to the at least one macromolecule;
incorporating the substrate in a sample;
measuring through a magnetic based detection method a magnetic property of the sample to obtain a first measurement;
measuring, through the magnetic based detection method and after obtaining the first measurement, a magnetic property of the sample to obtain a second measurement;
comparing the first measurement to the second measurement; and
determining there is degradation of the substrate by an enzyme in the sample if there is a change between the first measurement and the second measurement;
wherein said change is indicative of at least one of (a) aggregation of said plurality of magnetic particles, (b) dispersion of said plurality of magnetic particles, (c) a change in the size of said plurality of magnetic particles, and (d) a change in the size of said substrate.

20. A method for detecting the activity of at least one enzyme in a sample, consisting of the steps in order:
selecting at least one macromolecule, wherein at least one of the at least one macromolecule is selected from the group consisting of a protein, a polypeptide, a modified protein, a modified polypeptide, a glycoprotein, a lipoprotein, collagen, one or more collagen fragments, a mixture of collagen with one or more collagen fragments, and gelatin;
forming a substrate, the substrate is a plurality of magnetic particles covalently bound, by means of a process that involves silanization, to the at least one macromolecule;
incorporating the substrate in the sample;
measuring through a nuclear magnetic resonance-based detection method a T1 or T2 relaxation time of the sample to obtain a first measurement;
measuring, through the nuclear magnetic resonance-based detection method and after obtaining the first measurement, the T1 or T2 relaxation time of the sample to obtain a second measurement;
comparing the first measurement to the second measurement; and
determining there is an aggregation of the magnetic particles as a consequence of enzymatic digestion of the substrate thus indicating the presence of enzymatic activity in the sample.

* * * * *